(12) United States Patent
Yagi et al.

(10) Patent No.: US 7,113,828 B2
(45) Date of Patent: Sep. 26, 2006

(54) VISUAL RESTORATION AIDING DEVICE

(75) Inventors: Toru Yagi, Nagoya (JP); Hiroyuki Tashiro, Nukata-gun (JP); Yasuo Terasawa, Obu (JP)

(73) Assignee: Nidek Co., Ltd., Gamagori (JP)

( * ) Notice: Subject to any disclaimer, the term of this patent is extended or adjusted under 35 U.S.C. 154(b) by 74 days.

(21) Appl. No.: 10/806,210

(22) Filed: Mar. 23, 2004

(65) Prior Publication Data

US 2004/0193232 A1    Sep. 30, 2004

(30) Foreign Application Priority Data

Mar. 31, 2003   (JP)   ............... 2003-093084

(51) Int. Cl.
    *A61N 1/08*    (2006.01)
(52) U.S. Cl. ....................................... 607/54
(58) Field of Classification Search ............... 607/53, 607/54, 60; 623/6.63, 4.1
    See application file for complete search history.

(56) References Cited

U.S. PATENT DOCUMENTS 5,935,155 A * 8/1999 Humayun et al. ............ 607/54

FOREIGN PATENT DOCUMENTS

| JP | A 8-511697 | 12/1996 |
| JP | A 11-506662 | 6/1999 |
| JP | A 11-511248 | 9/1999 |
| WO | WO 90/00912 | 2/1990 |
| WO | WO 94/26209 | 11/1994 |
| WO | WO 96/39221 | 12/1996 |
| WO | WO 97/05922 | 2/1997 |

OTHER PUBLICATIONS http://www.integraltech.com/terminology.cfm ; Integral Technologies.*

* cited by examiner

*Primary Examiner*—Mark Bockelman
(74) *Attorney, Agent, or Firm*—Oliff & Berridge, PLC

(57) ABSTRACT

A visual restoration aiding device including an electrode array having a plurality of electrodes placed on or under a retina of an eye of the patient for applying an electrical stimulation pulse signal to cells constituting the retina; a photographing unit which photographs an object to be recognized by the patient; a converting unit which converts photographic data transmitted from the photographing unit to data for electrical stimulation pulse signals; and a control unit which outputs an electrical stimulation pulse signal through each electrode based on the data for electrical stimulation pulse signals so as not to simultaneously output the electrical stimulation pulse signals through electrodes arranged within a distance that electrical stimulation pulse signals outputted through the electrodes will interfere with each other and which switches between the electrodes used for outputting the electrical stimulation pulse signals and the electrodes unused for outputting the electrical stimulation pulse signals.

6 Claims, 6 Drawing Sheets ial restoration aiding device for restoring vision of a patient, comprising: an electrode array having a plurality of electrodes placed on or under a retina of an eye of the patient for applying an electrical stimulation pulse signal to cells constituting the retina; a photographing unit which photographs an object to be recognized by the patient; a converting unit which converts photographic data transmitted from the photographing unit to data for electrical stimulation pulse signals; and a control unit which outputs an electrical stimulation pulse signal through each electrode based on the data for electrical stimulation pulse signals, the control unit controlling the signal output so as not to simultaneously output the electrical stimulation pulse signals through electrodes arranged within a distance that electrical stimulation pulse signals outputted through the electrodes will interfere with each other and the control unit switching between the electrodes used for outputting the electrical stimulation pulse signals and the electrodes unused for outputting the electrical stimulation pulse signals.

VISUAL RESTORATION AIDING DEVICE

BACKGROUND OF THE INVENTION

1. Field of the Invention

The present invention relates to a visual restoration aiding device for inducing restoration of vision.

2. Description of Related Art

In recent years, research has been conducted about a visual restoration aiding device using an electrode or the like placed (implanted) in an eye to induce restoration of vision by electrically stimulating cells constituting a retina. For example, U.S. Pat. No. 5,935.155 teaches a visual restoration aiding device designed to convert an extracorporeally photographed visual image to an optical signal or an electromagnetic signal, transmit the converted signal into the eye, and then output (pass) an electrical stimulation pulse signal (a stimulating electric current) through the electrode to stimulate the cells constituting the retina to induce visual restoration. In the case of inducing visual restoration by the electrical stimulation pulse signal provided through the electrode, it is necessary to place as many electrodes as possible at a high density in order to provide clearer vision.

In a state in which the electrodes are arranged at high density, however, when the electrical stimulation pulse signals are simultaneously outputted through adjacent electrodes, those signals are likely to interfere with each other. Such interference would become a factor that hinders the visual restoration.

SUMMARY OF THE INVENTION

The present invention has been made in view of the above circumstance. It is an object to overcome the above problems and to provide a visual restoration aiding device which can properly induce restoration of vision while preventing electrical stimulation pulse signals from interfering with each other even when electrodes are arranged at high density.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a visu

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
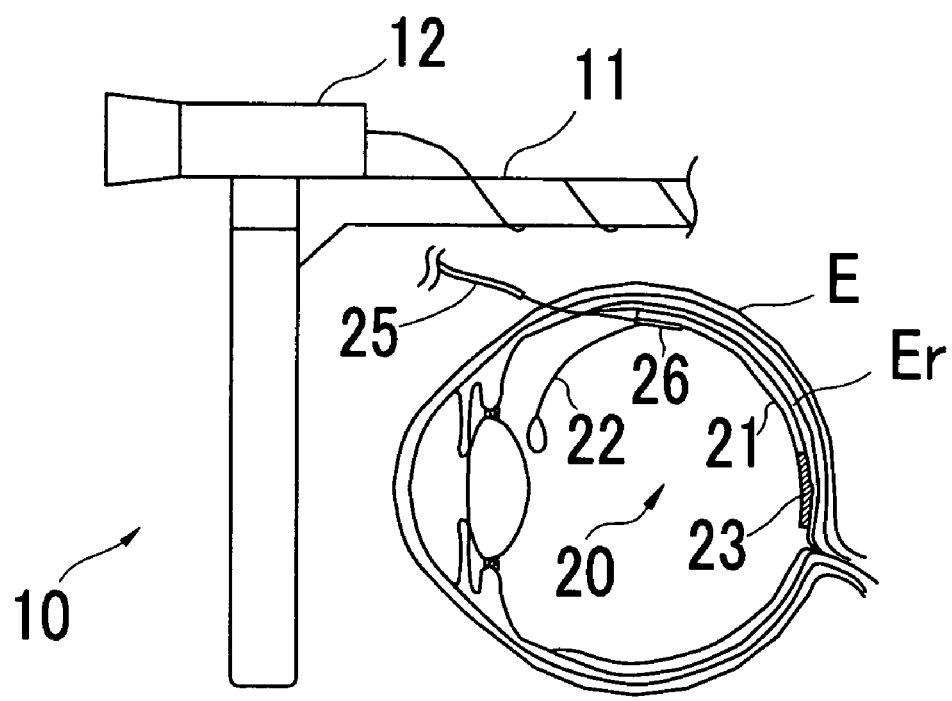
FIG. 1 is a schematic structural view of a visual restoration aiding device in an embodiment according to the present invention.
Figure 2:
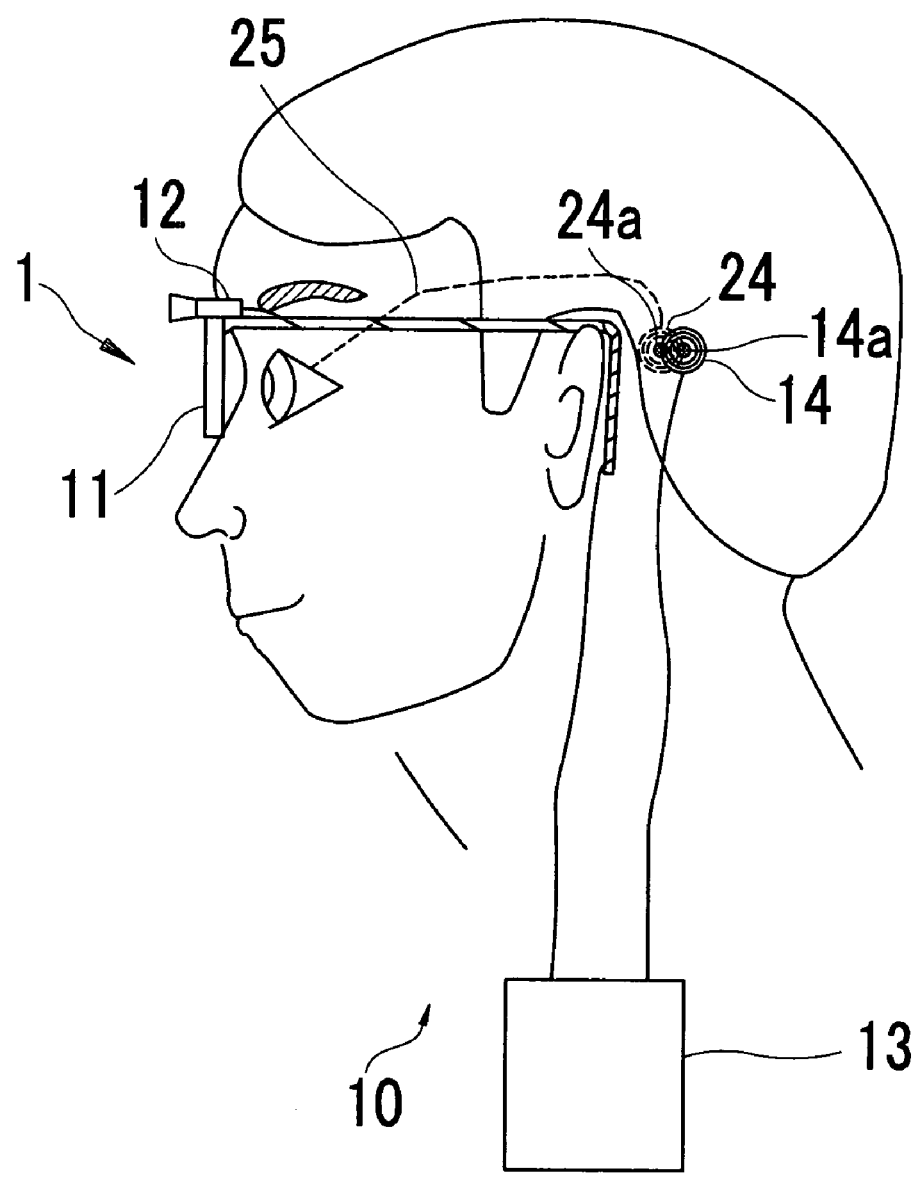
FIG. 2 is a schematic structural view of the visual restoration aiding device.
Figure 3:
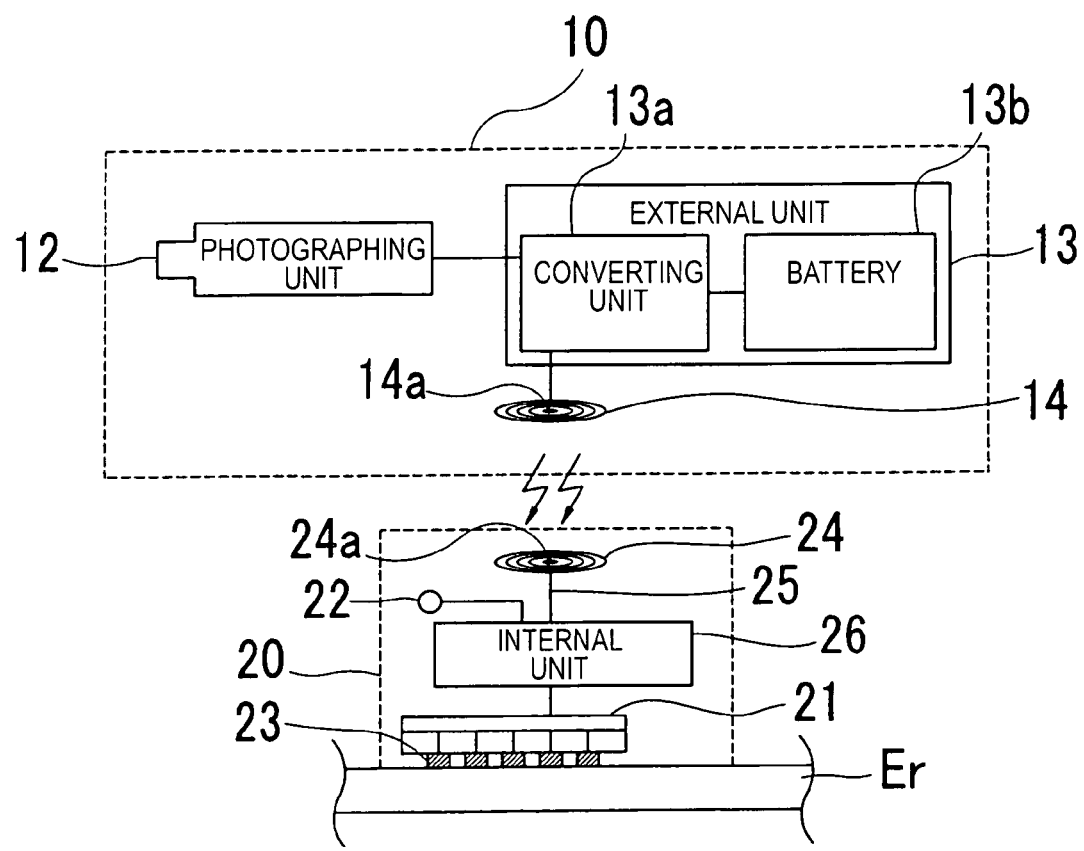
FIG. 3 is a block view showing a control system of the visual restoration aiding device.

A detailed description of a preferred embodiment of a visual restoration aiding device embodying the present invention will now be given referring to the accompanying drawings. FIGS. 1 and 2 are schematic views of the visual restoration aiding device in the present embodiment. FIG. 3 is a schematic block diagram of a control system in the device.

The visual restoration aiding device 1 includes an external (extracorporeal) device 10 which photographs the outside world, or captures surrounding images, and an internal (intracorporeal) device 20 which applies electrical stimulation to cells constituting a retina to induce restoration of vision. The external device 10 includes a visor 11 which a patient wears, a photographing unit 12 such as a CCD camera which is mounted on the visor 11, an external unit 13, and a transmitting unit 14 including a coil, as shown in FIGS. 1 and 2. The visor 11 is shaped like eyeglasses, which the patient wears in the front of his eye E. The photographing unit 12 is mounted in the front of the visor 11 and photographs an object to be recognized by the patient.

As shown in FIG. 3, the external unit 13 includes a pulse signal converting unit 13a for converting photographic data (video data) transmitted from the photographing unit 12 to data (information) for electrical stimulation pulse signals and a battery 13b for supplying electric power to the visual restoration aiding device 1 (that is, the external device 10 and the internal device 20). The transmitting unit 14 is used for transmitting the converted data for electrical stimulation pulse signals by the converting unit 13a and the electric power for driving the internal device 20, in the form of electromagnetic waves, to the internal device 20 by wireless communication. The transmitting unit 14 is provided at its center with a magnet 14a. This magnet 14a is used for enhancing the transmitting efficiency of the transmitting unit 14 and also to fit the position of the transmitting unit 14 to a receiving unit 24 mentioned later.

The internal device 20 includes a substrate 21 on which electrodes 23 are placed for applying the electrical stimulation pulse signals to the cells constituting the retina Er of the eye E, an indifferent electrode 22, the receiving unit 24 including a coil for receiving the electromagnetic waves from the external device 10, a cable 25, and an internal unit 26. The receiving unit 24 is provided at its center with a magnet 24*a* which is used for the same purpose as the magnet 14*a* of the transmitting unit 14.

Figure 4A:
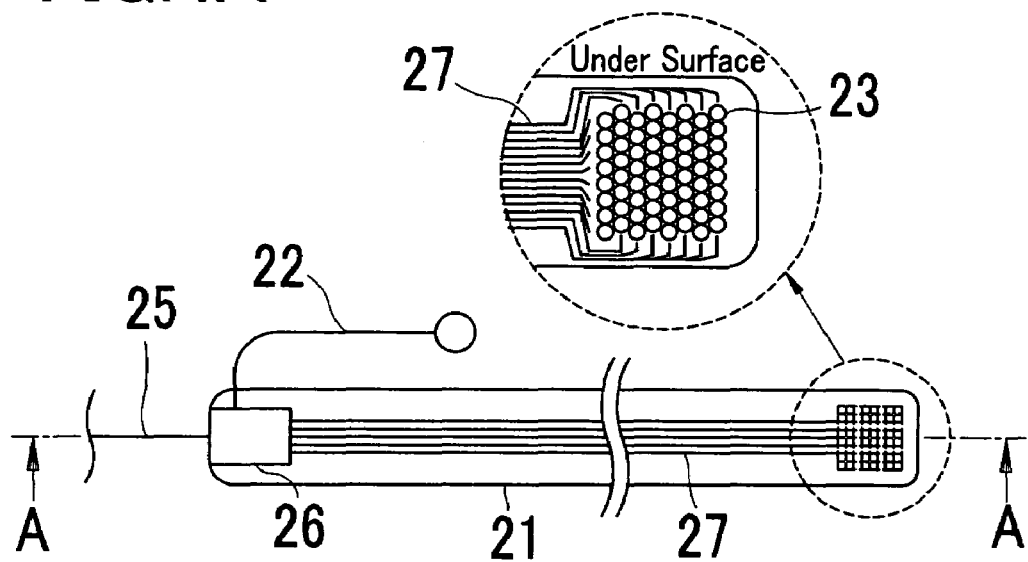
FIG. 4A is a plan view of an internal device.
Figure 4B:
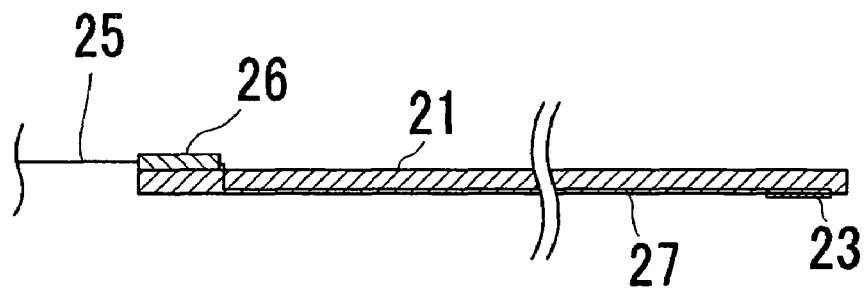
FIG. 4B is a cross-sectional view of the internal device taken along line A—A in FIG. 4A.

FIG. 4A is a plan view showing a schematic structure of the internal device 20 and FIG. 4B is a cross-sectional view of the internal device 20 taken along line A—A in FIG. 4A.

The substrate 21 is made of a flexible material having good biocompatibility, which is polyimide in the present embodiment. The substrate 21 is of a substantially long plate shape whose end (right end in FIG. 4A) is provided, on the under surface of the substrate 21 (i.e., on the back of the drawing sheet of FIG. 4A), with a multipoint electrode array having a plurality of electrodes 23 arranged at predetermined intervals (at regular intervals) for applying the electrical stimulation pulse signals to the cells constituting the retina. The electrodes 23 are arranged in a honeycomb pattern in order to minimum the intervals between the electrodes 23 as shown in FIG. 4A, particularly, in a partially enlarged figure. This arrangement contributes to an increased electrode placement density, thereby achieving high spatial resolution. In the present embodiment, a total of sixty-four electrodes 23 in an 8×8 arrangement are placed on the substrate 21.

Each electrode 23 is independently connected with a corresponding electric wire (a lead wire) 27. As shown in FIG. 4B, each electric wire 27 connects between the associated electrode 23 and the internal unit 26 provided on the upper surface of the substrate 21 (i.e., on the front of the drawing sheet of FIG. 4A) at a base end (a left end in FIG. 4A) thereof. The internal unit 26 is also connected to the receiving unit 24 through the cable 25. This internal unit 26 includes a converting circuit for converting the data for electrical stimulation pulse signals transmitted via the receiving unit 24 to the electrical stimulation pulse signals and a control part which controls output of the electrical stimulation pulse signals through the electrodes 23.

To place (implant) the internal device 20 (the substrate 21) constructed as above in the eye E, it is fixedly attached to the retina Er of the eye E by a rivet-shaped tack not shown, adhesive having good biocompatibility, etc.

The following explanation is made on output control of the electrical stimulation pulse signals for visual restoration in the visual restoration aiding device constructed as above.

The external device 10 and the internal device 20 of the visual restoration aiding device 1 are attached to the eye E as shown in FIGS. 1 and 2.

The photographic data on an object photographed by the photographing unit 12 is converted by the signal converting unit 13*a* to the data for electrical stimulation pulse signals within a predetermined frequency band. The converted data is then transmitted in the form of electromagnetic waves by the transmitting unit 14 to the internal device 20. The data for electrical stimulation pulse signals includes the information about the electrodes 23 needed to output the electrical stimulation pulse signals and the stimulation conditions such as a frequency of the electrical stimulation pulse signals to be outputted through the electrodes 23, an amplitude (namely, intensity of stimulation electric currents), and a stimulating time length. Simultaneously, the signal converting unit 13*a* converts the electric power supplied from the battery 13*b* to an electric power signal of a frequency band different from the frequency band of the data for electrical stimulation pulse signals and transmits it in the form of electromagnetic waves to the internal device 20.

In the internal device 20, the receiving unit 24 receives the data for electrical stimulation pulse signals and the data for electric power transmitted from the external device 10 and then transmits them to the internal unit 26. This internal unit 26 extracts a signal of the frequency band being used for the data for electrical stimulation pulse signals from among the received signals. A signal of another frequency band is supplied as the electric power for driving the internal device 20. The internal unit 26 forms electrical stimulation pulse signals to be outputted through the electrodes 23 based on the extracted data for electrical stimulation pulse signals and output those signals through the electrodes 23, thereby inducing the restoration of vision.

At this time, the internal unit 26 effects control of signal output through the electrodes 23 so that the electrical stimulation pulse signals are not simultaneously outputted through adjacent electrodes of the electrodes 23. The internal unit 26 outputs the electrical stimulation pulse signals through the electrodes 23 in turn while switching between the electrodes used for outputting the electrical stimulation pulse signals and the electrodes unused for outputting the electrical stimulation pulse signals. The internal unit 26 performs such control in a short time, thereby outputting the electrical stimulation pulse signals through all the electrodes 23 needed to output the electrical stimulation pulse signals for allowing the patient to recognize the object.

FIGS. 5A to 5D show an example of the output control to be executed by the internal unit 26 to output the stimulation pulse signals through each electrode 23 in turn. With reference to these figures, explanation is made on the case where sixteen electrodes 23 placed in a 4×4 arrangement (in a honeycomb pattern) are used. In relation to the shown electrode arrangement, it is thought that the stimulation pulse signals simultaneously outputted through adjacent electrodes will interfere with each other, whereas the stimulation pulse signals simultaneously outputted through unadjacent electrodes will not interfere with each other. Alphabets and numerals in the figures are used for specifying respective positions (addresses) of sixteen electrodes 23.

Figure 5A:
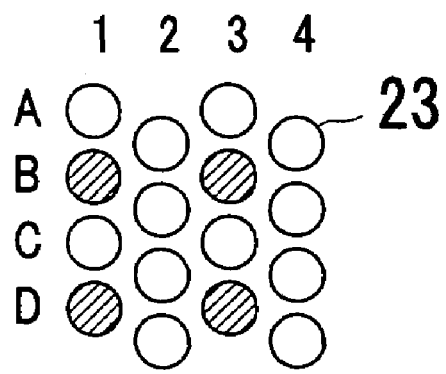
FIGS. 5A to 5D show an example of output control of electrodes.
Figure 5C:
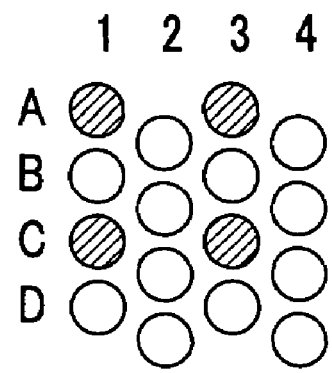
Figure 5B:
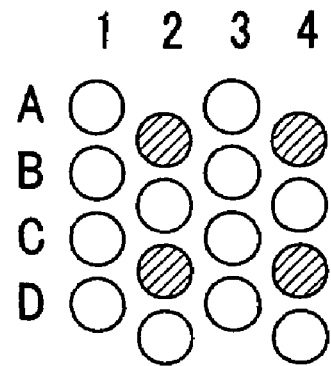
Figure 5D:
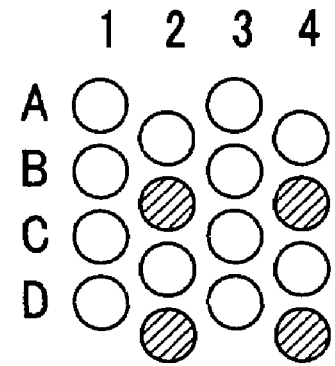

As shown in FIG. 5A, the internal unit 26 outputs the electrical stimulation pulse signals simultaneously through the electrodes 23 at addresses of B1, B3, D1, and D3, which are illustrated with hatched lines. It is to be noted that the electrodes 23 through which the electrical stimulation pulse signals are first outputted are not limited to the above electrodes 23 at B1, B3, D1, and D3 but required to be unadjacent so that the electrical stimulation pulse signals are not outputted simultaneously through adjacent electrodes 23. After the electrical stimulation pulse signals are outputted through the electrodes 23 at B1, B3, D1, and D3 for a duration needed to stimulate the cells constituting the retina, the internal unit 26 stops the output of the electrical stimulation pulse signals through the electrodes 23 at B1, B3, D1, and D3. Then, the internal unit 26 similarly outputs the electrical stimulation pulse signals simultaneously through unadjacent electrodes 23 (at A2, A4, C2, and C4) other than the electrodes 23 at B1, B3, D1, and D3, as shown in FIG. 5B. After the output of the electrical stimulation pulse signals through the electrodes 23 at A2, A4, C2, and C4, the internal unit 26 outputs the electrical stimulation pulse signals through the electrodes 23 at A1, A3, C1, and C3 as shown in FIG. 5C. After that, the internal unit 26 outputs the electrical stimulation pulse signals through the electrodes 23 at B2, B4, D2, and D4, as shown in FIG. 5D. The output of the electrical stimulation pulse signals through all the electrodes 23 is thus completed. To allow a patient to recognize an object, the internal unit 26 outputs the signals through the electrodes 23 in a time division manner and switches (changes), with the lapse of time, the electrodes 23 used for outputting the electrical stimulation pulse signals. Consequently, the electrical stimulation pulse signals are not outputted simultaneously through the electrodes arranged (adjacently in the present embodiment) within a distance (interval) that the stimulation pulse signals outputted through such electrodes will interfere with each other. The stimulating electric currents can be prevented from interfering each other, so that restoration of vision can be achieved properly. The electrodes unused for outputting the electrical stimulation pulse signals may be kept in a high impedance condition or an insulated condition.

For one recognition of an object, the switching of the electrodes 23 used for outputting the signals has to be fully completed within a duration during which the patient can recognize one (one-frame) object by a total sum of the electrical stimulation pulse signals outputted in a time division manner. The duration to simultaneously output the electrical stimulation pulse signals through the unadjacent electrodes 23 is set to at least a duration needed to stimulate the cells constituting the retina by the electrical stimulation pulse signals (a duration needed to allow the patient to sense vision).

In order to allow the patient to recognize a moving image without frame dropouts, the converting rate of the object to be recognized is preferably 24 to 30 frames or more (24 to 30 Hz or more) per second as with a frame rate for a movie. Accordingly, to allow the patient to recognize the object of one frame, it is preferable to fully complete the output of the electrical stimulation pulse signals through the associated electrodes 23 in $1/30$ second to $1/24$ second.

Based on the above conditions, the internal unit 26 controls the output of the electrical stimulation pulse signals through each electrode 23.

In the present embodiment, the electric wires 27 are connected in one-to-one correspondence with the electrodes 23. In this case, as the number of electrodes 23 formed on the substrate 21 is increased, the more electric wires need to be provided. This may cause a disadvantage to miniaturization of the internal device 20. In the case that a large number of electrodes 23 are needed, they are preferably provided on a wiring circuit using an active matrix system. Accordingly, the number of electric wires 27 is small, whereas the number of electrodes 23 can be increased.

Figure 6:
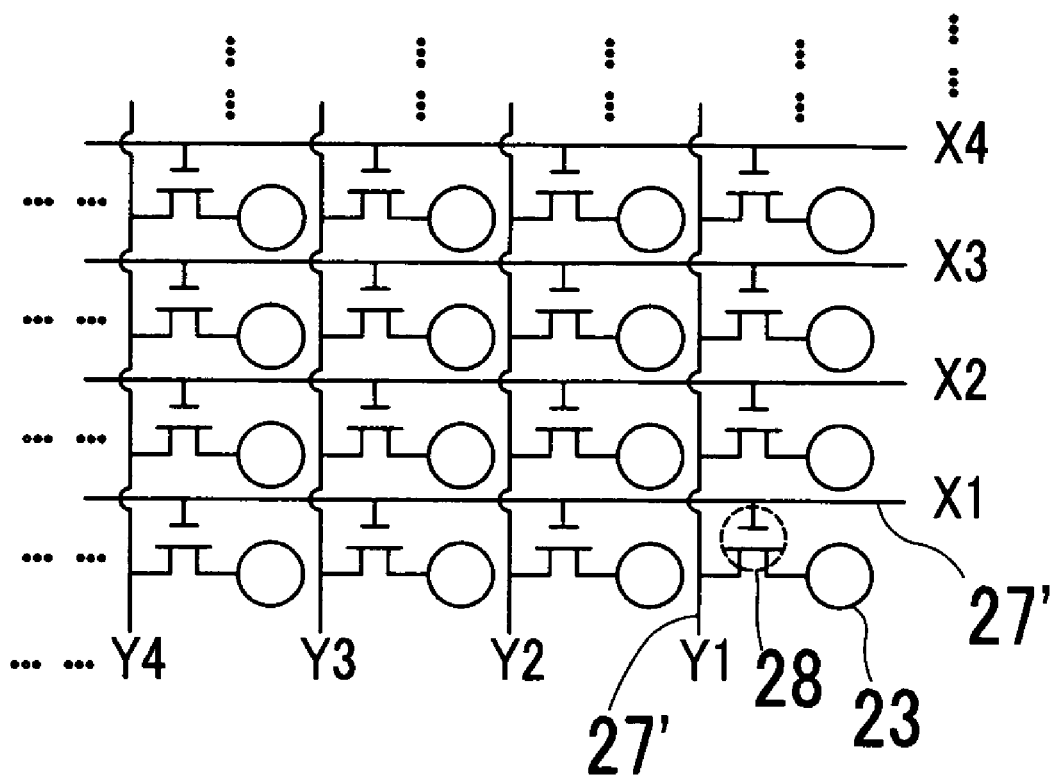
FIG. 6 is a schematic structural view of an electrode array having a wiring circuit in an active matrix system.

FIG. 6 is a schematic structural view of an electrode array having the wiring circuit of the active matrix system. Electric wires 27' are arranged in a grid pattern at the end of the substrate 21 where the electrodes 23 are placed. An active element 28, which is a thin transistor, is placed at each intersection point of the electric wires 27'. One end of each of the active elements 28 is connected with the electrode 23.

The active elements 28 connected with the electrodes 23 are turned ON/OFF through the electric wires 27' (X-electrodes) placed in the X-coordinate (X1, X2, ... ) shown in FIG. 6. The active elements 28 in the ON state are able to maintain the voltage as is and communicate with the electric wires 27' (Y-electrodes) in the Y-coordinate (Y1, Y2, ... ). Thereafter, the electric wires 27' in the Y-coordinate are applied with voltage to cause the target electrodes 23 in the ON state to output the electrical stimulation pulse signals.

When such wiring circuit of the active matrix system is used, for example, sixteen electric wires 27' suffice for the sixty-four electrodes placed in the 8×8 arrangement in the present embodiment. Further, sixty-four electric wires 27' suffice for a thousand and twenty-four electrodes placed in a 32×32 arrangement.

As described above, the output control of the electrodes 23 by the internal unit 26 and the wiring circuit of the active matrix system may be combined. In this case, visual restoration can be achieved properly even when a multipoint electrode array formed of more electrodes is used.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A visual restoration aiding device for restoring vision of a patient, comprising:
    an electrode array having a plurality of electrodes which apply electrical stimulation pulse signals to cells constituting a retina of an eye of the patient, the electrodes including first electrodes and second electrodes;
    a photographing unit which photographs an object to be recognized by the patient to provide at least one photograph frame of the object;
    a converting unit which converts photographic data transmitted from the photographing unit to data for electrical stimulation pulse signals; and
    a control unit which outputs the electrical stimulation pulse signals through each electrode based on the data for electrical stimulation pulse signals,
    the control unit simultaneously outputting a portion of the electrical stimulation pulse signals only through the first electrodes during a first time period so as not to simultaneously output another portion of the electrical stimulation pulse signals through the second electrodes that are arranged within a distance from the first electrodes whereby the portion of the electrical stimulation pulse signals outputted through the first electrodes will not interfere with the another portion of the electrical stimulation pulse signals outputted through the second electrodes,
    the control unit switching from outputting the portion of the electrical stimulation pulse signals through the first electrodes to outputting the another portion of the electrical stimulation pulse signals through only the second electrodes during a second time period,
    the control unit completely terminating the outputting of the electrical stimulation pulse signals through all of the first and second electrodes whereby each photograph frame provided by the photographing unit results in electrical stimulation pulse signals applied to the first and second electrodes in a time division manner.

2. The visual restoration aiding device according to claim 1, wherein the control unit does not simultaneously output the electrical stimulation pulse signals through adjacent electrodes of the electrodes.

3. The visual restoration aiding device according to claim 1, wherein the control unit completely terminates the switching of the electrodes to be used for outputting the electrical stimulation pulse signals, within the duration needed for allowing the patient to recognize the object of one frame.

4. The visual restoration aiding device according to claim 3, wherein the control unit completely terminates the switching of the electrodes to be used for outputting the electrical stimulation pulse signals, in $1/30$ to $1/24$ second.

5. The visual restoration aiding device according to claim 1, wherein the electrode array has a wiring circuit of an active matrix system.

6. The visual restoration aiding device according to claim 1, wherein the electrode array has the electrodes arranged in a honeycomb pattern.

* * * * *